US007813808B1

(12) United States Patent
Doron et al.

(10) Patent No.: US 7,813,808 B1
(45) Date of Patent: Oct. 12, 2010

(54) IMPLANTED SENSOR SYSTEM WITH OPTIMIZED OPERATIONAL AND SENSING PARAMETERS

(75) Inventors: Eyal Doron, Kiryat Yam (IL); Boaz Rippin, Belt Yehoshua (IL)

(73) Assignee: Remon Medical Technologies Ltd, St. Paul, MN (US)

( * ) Notice: Subject to any disclaimer, the term of this patent is extended or adjusted under 35 U.S.C. 154(b) by 31 days.

(21) Appl. No.: 11/287,516

(22) Filed: Nov. 23, 2005

Related U.S. Application Data

(60) Provisional application No. 60/630,910, filed on Nov. 24, 2004.

(51) Int. Cl.
*A61N 1/02* (2006.01)
(52) U.S. Cl. ...................................................... 607/59
(58) Field of Classification Search ................ 600/510; 607/30, 59, 23
See application file for complete search history.

(56) References Cited

U.S. PATENT DOCUMENTS

| | | | |
|---|---|---|---|
| 3,310,885 A | 3/1967 | Alderson |
| 3,320,946 A | 5/1967 | Dethloff et al. |
| 3,536,836 A | 10/1970 | Pfeiffer |
| 3,568,661 A | 3/1971 | Franklin |
| 3,672,352 A | 6/1972 | Summers |
| 3,692,027 A | 9/1972 | Ellinwood |
| 3,757,770 A | 9/1973 | Brayshaw et al. |
| 3,794,840 A | 2/1974 | Scott |
| 3,868,578 A | 2/1975 | Oldham |
| 3,943,915 A | 3/1976 | Severson |
| 4,003,379 A | 1/1977 | Ellinwood |
| 4,041,954 A | 8/1977 | Ohara |
| 4,127,110 A | 11/1978 | Bullara |
| 4,146,029 A | 3/1979 | Ellinwood |
| 4,223,801 A | 9/1980 | Carlson |
| 4,227,407 A | 10/1980 | Drost |
| 4,237,900 A | 12/1980 | Schulman et al. |
| 4,281,664 A | 8/1981 | Duggan |
| 4,360,019 A | 11/1982 | Portner et al. |
| 4,407,296 A | 10/1983 | Anderson |
| 4,450,527 A | 5/1984 | Sramek |
| 4,480,483 A | 11/1984 | McShane |
| 4,519,401 A | 5/1985 | Ko et al. |

(Continued)

FOREIGN PATENT DOCUMENTS

EP        0897690        2/1999

(Continued)

OTHER PUBLICATIONS

B. C. Penney et al., "Simplified electrode array for impedance cardiography," Medical & Biological Engineering & Computing, 1985, 23, p. 1-7.

(Continued)

*Primary Examiner*—Carl H Layno
*Assistant Examiner*—Amanda Patton
(74) *Attorney, Agent, or Firm*—Faegre & Benson LLP

(57) ABSTRACT

A medical system includes an implantable sensor; and a medical device having a communication link with the sensor. The medical device further including a controller, wherein operating parameters for controlling sampling of a physiological characteristic or other parameter by the implantable sensor are calculated by the controller and communicated to the sensor dynamically.

19 Claims, 4 Drawing Sheets

U.S. PATENT DOCUMENTS

| | | | |
|---|---|---|---|
| 4,541,431 A | 9/1985 | Ibrahim et al. | |
| 4,543,955 A * | 10/1985 | Schroeppel | 600/348 |
| 4,550,370 A | 10/1985 | Baker | |
| 4,583,553 A | 4/1986 | Shah et al. | |
| 4,585,004 A | 4/1986 | Brownlee | |
| 4,593,703 A | 6/1986 | Cosman | |
| 4,600,855 A | 7/1986 | Strachan | |
| 4,616,640 A | 10/1986 | Kaali et al. | |
| 4,651,740 A | 3/1987 | Schroeppel | |
| 4,653,508 A | 3/1987 | Cosman | |
| 4,660,568 A | 4/1987 | Cosman | |
| 4,676,255 A | 6/1987 | Cosman | |
| 4,677,985 A | 7/1987 | Bro et al. | |
| 4,680,957 A | 7/1987 | Dodd | |
| 4,686,987 A | 8/1987 | Salo et al. | |
| 4,697,595 A | 10/1987 | Breyer et al. | |
| 4,716,903 A | 1/1988 | Hansen et al. | |
| 4,719,921 A | 1/1988 | Chirife | |
| 4,726,380 A | 2/1988 | Vollmann et al. | |
| 4,768,176 A | 8/1988 | Kehr et al. | |
| 4,768,177 A | 8/1988 | Kehr et al. | |
| 4,781,715 A | 11/1988 | Wurzel | |
| 4,791,936 A | 12/1988 | Snell et al. | |
| 4,793,827 A | 12/1988 | Kovacs et al. | |
| 4,809,697 A | 3/1989 | Causey, III et al. | |
| 4,814,974 A | 3/1989 | Narayanan et al. | |
| 4,845,503 A | 7/1989 | Adam et al. | |
| 4,846,191 A | 7/1989 | Brockway et al. | |
| 4,854,327 A | 8/1989 | Kunig | |
| 4,899,752 A | 2/1990 | Cohen | |
| 4,909,259 A | 3/1990 | Tehrani | |
| 4,920,489 A | 4/1990 | Hubelbank et al. | |
| 4,945,477 A | 7/1990 | Edwards | |
| 4,945,914 A | 8/1990 | Allen | |
| 4,967,749 A | 11/1990 | Cohen | |
| 4,986,270 A | 1/1991 | Cohen | |
| 4,991,579 A | 2/1991 | Allen | |
| 4,995,068 A | 2/1991 | Chou et al. | |
| 4,995,398 A | 2/1991 | Turnidge | |
| 5,002,062 A | 3/1991 | Suzuki | |
| 5,003,976 A | 4/1991 | Alt | |
| 5,007,431 A | 4/1991 | Donehoo, III | |
| 5,024,224 A | 6/1991 | Engebretson | |
| 5,025,795 A | 6/1991 | Kunig | |
| 5,029,582 A | 7/1991 | Lekholm | |
| 5,040,536 A | 8/1991 | Riff | |
| 5,040,538 A | 8/1991 | Mortazavi | |
| 5,052,399 A | 10/1991 | Olive et al. | |
| 5,113,859 A | 5/1992 | Funke | |
| 5,154,171 A | 10/1992 | Chirife | |
| 5,161,536 A | 11/1992 | Vilkomerson et al. | |
| 5,163,429 A * | 11/1992 | Cohen | 607/4 |
| 5,178,151 A | 1/1993 | Sackner | |
| 5,178,153 A | 1/1993 | Einzig | |
| 5,183,051 A | 2/1993 | Kraidin et al. | |
| 5,190,035 A | 3/1993 | Salo et al. | |
| 5,199,428 A | 4/1993 | Obel et al. | |
| 5,200,891 A | 4/1993 | Kehr et al. | |
| 5,213,098 A | 5/1993 | Bennett et al. | |
| 5,215,098 A | 6/1993 | Steinhaus et al. | |
| 5,217,021 A | 6/1993 | Steinhaus et al. | |
| 5,246,008 A | 9/1993 | Mueller | |
| 5,263,486 A * | 11/1993 | Jeffreys | 600/508 |
| 5,265,615 A | 11/1993 | Frank et al. | |
| 5,267,174 A | 11/1993 | Kaufman et al. | |
| 5,277,191 A | 1/1994 | Hughes | |
| 5,279,309 A | 1/1994 | Taylor et al. | |
| 5,279,607 A | 1/1994 | Schentag et al. | |
| 5,289,821 A | 3/1994 | Swartz | |
| 5,300,092 A * | 4/1994 | Schaldach | 607/18 |
| 5,309,919 A | 5/1994 | Snell et al. | |
| 5,312,446 A | 5/1994 | Holschbach et al. | |
| 5,313,953 A | 5/1994 | Yomtov et al. | |
| 5,314,457 A | 5/1994 | Jeutter et al. | |
| 5,329,459 A | 7/1994 | Kaufman et al. | |
| 5,330,505 A | 7/1994 | Cohen | |
| 5,331,966 A | 7/1994 | Bennett et al. | |
| 5,339,051 A | 8/1994 | Koehler et al. | |
| 5,354,316 A | 10/1994 | Keimel | |
| 5,360,440 A | 11/1994 | Andersen | |
| 5,368,040 A | 11/1994 | Carney | |
| 5,375,603 A | 12/1994 | Feiler | |
| 5,394,457 A | 2/1995 | Leibinger et al. | |
| 5,397,329 A | 3/1995 | Allen | |
| 5,400,793 A | 3/1995 | Wesseling | |
| 5,411,535 A | 5/1995 | Fujii et al. | |
| 5,411,551 A | 5/1995 | Winston et al. | |
| 5,417,717 A | 5/1995 | Salo et al. | |
| 5,423,323 A | 6/1995 | Orth | |
| 5,423,334 A | 6/1995 | Jordan | |
| 5,438,990 A | 8/1995 | Wahlstrand et al. | |
| 5,442,351 A | 8/1995 | Horspool et al. | |
| 5,445,608 A | 8/1995 | Chen et al. | |
| 5,454,838 A | 10/1995 | Vallana et al. | |
| 5,458,627 A | 10/1995 | Baranowski, Jr. et al. | |
| 5,469,859 A | 11/1995 | Tsoglin et al. | |
| 5,476,488 A | 12/1995 | Morgan et al. | |
| 5,488,954 A | 2/1996 | Sleva et al. | |
| 5,490,962 A | 2/1996 | Cima et al. | |
| 5,507,780 A | 4/1996 | Finch | |
| 5,509,424 A | 4/1996 | Al Ali | |
| 5,518,001 A | 5/1996 | Snell | |
| 5,528,067 A | 6/1996 | Farb | |
| 5,535,752 A | 7/1996 | Halperin et al. | |
| 5,545,186 A | 8/1996 | Olson et al. | |
| 5,558,091 A | 9/1996 | Acker et al. | |
| 5,562,714 A | 10/1996 | Grevious | |
| 5,564,434 A | 10/1996 | Halperin et al. | |
| 5,571,152 A | 11/1996 | Chen et al. | |
| 5,603,331 A | 2/1997 | Heemels et al. | |
| 5,604,531 A | 2/1997 | Iddan et al. | |
| 5,619,997 A | 4/1997 | Kaplan | |
| 5,623,935 A | 4/1997 | Faisandier | |
| 5,626,630 A | 5/1997 | Markowitz et al. | |
| 5,628,782 A | 5/1997 | Myers | |
| 5,642,731 A | 7/1997 | Kehr | |
| 5,643,327 A | 7/1997 | Dawson et al. | |
| 5,647,369 A | 7/1997 | Petrucelli et al. | |
| 5,656,428 A | 8/1997 | McAllister et al. | |
| 5,704,352 A | 1/1998 | Tremblay et al. | |
| 5,705,753 A | 1/1998 | Hastings et al. | |
| 5,709,216 A | 1/1998 | Woodson, III | |
| 5,728,281 A | 3/1998 | Holstrom et al. | |
| 5,729,129 A | 3/1998 | Acker | |
| 5,732,708 A | 3/1998 | Nau et al. | |
| 5,733,313 A | 3/1998 | Barreras, Sr. et al. | |
| 5,735,887 A | 4/1998 | Barreras, Sr. et al. | |
| 5,741,316 A | 4/1998 | Chen et al. | |
| 5,749,909 A | 5/1998 | Schroeppel et al. | |
| 5,752,235 A | 5/1998 | Kehr et al. | |
| 5,752,976 A | 5/1998 | Duffin et al. | |
| 5,755,766 A | 5/1998 | Chastain et al. | |
| 5,769,877 A | 6/1998 | Barreras, Sr. | |
| 5,772,999 A | 6/1998 | Greenblatt et al. | |
| 5,776,168 A | 7/1998 | Gunderson | |
| 5,776,324 A | 7/1998 | Usala | |
| 5,779,634 A | 7/1998 | Ema et al. | |
| 5,785,660 A | 7/1998 | van Lake et al. | |
| 5,792,195 A | 8/1998 | Carlson et al. | |
| 5,796,827 A | 8/1998 | Coppersmith et al. | |
| 5,797,395 A | 8/1998 | Martin | |
| 5,797,898 A | 8/1998 | Santini, Jr. et al. | |
| 5,800,478 A | 9/1998 | Chen et al. | |
| 5,804,258 A | 9/1998 | Lohwasser et al. | |

| | | | |
|---|---|---|---|
| 5,807,258 A | 9/1998 | Cimochowski et al. | |
| 5,807,395 A | 9/1998 | Mulier et al. | |
| 5,807,397 A | 9/1998 | Barreras | |
| 5,810,009 A | 9/1998 | Mine et al. | |
| 5,810,735 A | 9/1998 | Halperin et al. | |
| 5,819,740 A | 10/1998 | Muhlenberg et al. | |
| 5,832,924 A | 11/1998 | Archibald et al. | |
| 5,833,603 A | 11/1998 | Kovacs et al. | |
| 5,833,715 A | 11/1998 | Vachon et al. | |
| 5,835,455 A | 11/1998 | Hanson et al. | |
| 5,836,300 A | 11/1998 | Mault | |
| 5,836,889 A | 11/1998 | Wyborny et al. | |
| 5,836,982 A | 11/1998 | Muhlenberg et al. | |
| 5,843,089 A | 12/1998 | Sahatjian et al. | |
| 5,843,135 A | 12/1998 | Weijand et al. | |
| 5,855,609 A | 1/1999 | Knapp | |
| 5,856,722 A | 1/1999 | Haronian et al. | |
| 5,868,673 A | 2/1999 | Vesely | |
| 5,873,835 A | 2/1999 | Hastings et al. | |
| 5,873,904 A | 2/1999 | Ragheb et al. | |
| 5,880,661 A | 3/1999 | Davidson et al. | |
| 5,886,267 A | 3/1999 | Ortiz | |
| 5,891,180 A | 4/1999 | Greeninger et al. | |
| 5,904,708 A | 5/1999 | Goedeke et al. | |
| 5,908,392 A | 6/1999 | Wilson et al. | |
| 5,911,685 A | 6/1999 | Siess et al. | |
| 5,919,221 A | 7/1999 | Miesel | |
| 5,935,081 A | 8/1999 | Kadhiresan | |
| 5,938,903 A | 8/1999 | Broderick | |
| 5,941,249 A | 8/1999 | Maynard | |
| 5,951,458 A | 9/1999 | Hastings et al. | |
| 5,954,641 A | 9/1999 | Kehr et al. | |
| 5,957,950 A | 9/1999 | Mockros et al. | |
| 5,967,986 A | 10/1999 | Cimochowski et al. | |
| 5,976,169 A | 11/1999 | Imran | |
| 5,979,898 A | 11/1999 | Pan | |
| 5,980,554 A | 11/1999 | Lenker et al. | |
| 6,002,963 A * | 12/1999 | Mouchawar et al. | 607/18 |
| 6,009,472 A | 12/1999 | Boudou et al. | |
| 6,021,347 A | 2/2000 | Herbst et al. | |
| 6,023,641 A | 2/2000 | Thompson | |
| 6,024,704 A | 2/2000 | Meador et al. | |
| 6,050,951 A * | 4/2000 | Friedman et al. | 600/485 |
| 6,053,873 A | 4/2000 | Govari et al. | |
| 6,080,190 A | 6/2000 | Schwartz | |
| 6,083,248 A | 7/2000 | Thompson | |
| 6,112,116 A | 8/2000 | Fischell et al. | |
| 6,123,861 A | 9/2000 | Santini, Jr. et al. | |
| 6,140,740 A | 10/2000 | Porat et al. | |
| 6,141,588 A | 10/2000 | Cox et al. | |
| 6,152,885 A | 11/2000 | Taepke | |
| 6,155,267 A | 12/2000 | Nelson | |
| 6,161,032 A | 12/2000 | Acker | |
| 6,162,238 A | 12/2000 | Kaplan et al. | |
| 6,164,284 A | 12/2000 | Schulman et al. | |
| 6,170,488 B1 | 1/2001 | Spillman, Jr. et al. | |
| 6,171,252 B1 | 1/2001 | Roberts | |
| 6,179,767 B1 | 1/2001 | Ziegler et al. | |
| 6,185,452 B1 | 2/2001 | Schulman et al. | |
| 6,185,455 B1 | 2/2001 | Loeb et al. | |
| 6,185,457 B1 | 2/2001 | Kroll et al. | |
| 6,198,965 B1 | 3/2001 | Penner et al. | |
| 6,200,265 B1 | 3/2001 | Walsh et al. | |
| 6,201,991 B1 | 3/2001 | Chekanov | |
| 6,206,914 B1 | 3/2001 | Soykan et al. | |
| 6,227,078 B1 | 5/2001 | Lemmo, Jr. | |
| 6,234,973 B1 | 5/2001 | Meador et al. | |
| 6,236,889 B1 | 5/2001 | Soykan et al. | |
| 6,237,398 B1 | 5/2001 | Porat et al. | |
| 6,239,724 B1 | 5/2001 | Doron et al. | |
| 6,248,080 B1 | 6/2001 | Miesel et al. | |
| 6,253,260 B1 | 6/2001 | Beardsley et al. | |
| 6,256,538 B1 | 7/2001 | Ekwall | |
| 6,266,567 B1 | 7/2001 | Ishikawa et al. | |
| 6,273,904 B1 | 8/2001 | Chen et al. | |
| 6,277,078 B1 | 8/2001 | Porat et al. | |
| 6,278,894 B1 | 8/2001 | Salo et al. | |
| 6,287,332 B1 | 9/2001 | Bolz et al. | |
| 6,305,381 B1 | 10/2001 | Weijand et al. | |
| 6,308,099 B1 | 10/2001 | Fox et al. | |
| 6,314,323 B1 | 11/2001 | Ekwall | |
| 6,330,957 B1 | 12/2001 | Bell-Greenstreet | |
| 6,331,163 B1 | 12/2001 | Kaplan | |
| 6,347,245 B1 | 2/2002 | Lee et al. | |
| 6,366,808 B1 | 4/2002 | Schroeppel et al. | |
| 6,368,275 B1 | 4/2002 | Sliwa et al. | |
| 6,397,661 B1 | 6/2002 | Grimes et al. | |
| 6,409,674 B1 * | 6/2002 | Brockway et al. | 600/486 |
| 6,409,675 B1 | 6/2002 | Turcott | |
| 6,411,850 B1 | 6/2002 | Kay et al. | |
| 6,416,474 B1 | 7/2002 | Penner et al. | |
| 6,431,175 B1 | 8/2002 | Penner et al. | |
| 6,432,050 B1 | 8/2002 | Porat et al. | |
| 6,438,408 B1 | 8/2002 | Mulligan et al. | |
| 6,441,747 B1 | 8/2002 | Khair et al. | |
| 6,442,413 B1 | 8/2002 | Silver | |
| 6,445,953 B1 | 9/2002 | Bulkes et al. | |
| 6,456,883 B1 | 9/2002 | Torgerson et al. | |
| 6,471,645 B1 | 10/2002 | Warkentin et al. | |
| 6,472,991 B1 | 10/2002 | Schulman et al. | |
| 6,475,170 B1 | 11/2002 | Doron et al. | |
| 6,486,588 B2 | 11/2002 | Doron et al. | |
| 6,504,286 B1 | 1/2003 | Porat et al. | |
| 6,522,914 B1 | 2/2003 | Huvelle et al. | |
| 6,526,314 B1 | 2/2003 | Eberle et al. | |
| 6,567,700 B1 | 5/2003 | Turcott et al. | |
| 6,574,510 B2 | 6/2003 | Von Arx et al. | |
| 6,580,946 B2 | 6/2003 | Struble | |
| 6,584,349 B1 | 6/2003 | Sage et al. | |
| 6,584,354 B1 | 6/2003 | Mann et al. | |
| 6,585,764 B2 | 7/2003 | Wright et al. | |
| 6,589,187 B1 | 7/2003 | Dirnberger et al. | |
| 6,599,242 B1 | 7/2003 | Splett et al. | |
| 6,604,000 B2 | 8/2003 | Lu | |
| 6,607,485 B2 | 8/2003 | Bardy | |
| 6,609,023 B1 | 8/2003 | Fischell et al. | |
| 6,615,083 B2 | 9/2003 | Kupper | |
| 6,622,049 B2 | 9/2003 | Penner et al. | |
| 6,622,050 B2 | 9/2003 | Thompson | |
| 6,628,985 B2 | 9/2003 | Sweeney et al. | |
| 6,628,989 B1 | 9/2003 | Penner et al. | |
| 6,638,231 B2 | 10/2003 | Govari et al. | |
| 6,644,322 B2 | 11/2003 | Webb | |
| 6,650,939 B2 | 11/2003 | Taepke, II et al. | |
| 6,654,638 B1 | 11/2003 | Sweeney | |
| 6,660,034 B1 | 12/2003 | Mandrusov et al. | |
| 6,675,049 B2 | 1/2004 | Thompson et al. | |
| 6,682,985 B2 | 1/2004 | Yuzuriha et al. | |
| 6,699,186 B1 | 3/2004 | Wolinsky et al. | |
| 6,702,847 B2 | 3/2004 | DiCarlo | |
| 6,708,061 B2 | 3/2004 | Salo et al. | |
| 6,708,065 B2 | 3/2004 | Von Arx et al. | |
| 6,712,772 B2 | 3/2004 | Cohen et al. | |
| 6,719,689 B2 | 4/2004 | Munneke et al. | |
| 6,720,709 B2 | 4/2004 | Porat et al. | |
| 6,720,887 B1 | 4/2004 | Zunti | |
| 6,738,667 B2 * | 5/2004 | Deno et al. | 607/23 |
| 6,738,671 B2 | 5/2004 | Christophersom et al. | |
| 6,743,173 B2 | 6/2004 | Penner et al. | |
| 6,754,795 B2 | 6/2004 | Chen et al. | |
| 6,758,822 B2 | 7/2004 | Romano | |
| 6,764,446 B2 | 7/2004 | Wolinsky et al. | |
| 6,778,859 B2 | 8/2004 | Gaindorge | |
| 6,782,810 B2 | 8/2004 | Vilo | |
| 6,783,499 B2 | 8/2004 | Schwartz | |
| 6,792,308 B2 | 9/2004 | Corbucci | |

| Patent No. | Date | Inventor |
|---|---|---|
| 6,792,311 B2 | 9/2004 | Fox et al. |
| 6,805,667 B2 | 10/2004 | Christopherson et al. |
| 6,809,507 B2 | 10/2004 | Morgan et al. |
| 6,823,210 B2 | 11/2004 | Eberle et al. |
| 6,824,512 B2 | 11/2004 | Warkentin et al. |
| 6,832,112 B1 | 12/2004 | Bornzin |
| 6,840,956 B1 | 1/2005 | Wolinsky et al. |
| 6,855,115 B2 | 2/2005 | Fonseca et al. |
| 6,859,665 B2 | 2/2005 | Ding et al. |
| 6,865,419 B2 | 3/2005 | Mulligan et al. |
| 6,868,346 B2 | 3/2005 | Larson et al. |
| 6,869,404 B2 | 3/2005 | Schulhauser et al. |
| 6,871,088 B2 | 3/2005 | Chinchoy |
| 6,885,889 B2 | 4/2005 | Chinchoy |
| 6,889,086 B2 | 5/2005 | Mass et al. |
| 6,895,265 B2 | 5/2005 | Silver |
| 6,907,285 B2 | 6/2005 | Denker et al. |
| 6,910,084 B2 | 6/2005 | Augustijn et al. |
| 6,915,162 B2 * | 7/2005 | Noren et al. ............... 607/23 |
| 6,926,670 B2 | 8/2005 | Rich et al. |
| 6,937,900 B1 | 8/2005 | Pianca et al. |
| 6,949,075 B2 | 9/2005 | Hatlestad et al. |
| 6,961,448 B2 | 11/2005 | Nichols et al. |
| 6,961,617 B1 | 11/2005 | Snell |
| 6,970,742 B2 | 11/2005 | Mann et al. |
| 6,978,182 B2 | 12/2005 | Mazar et al. |
| 6,985,773 B2 | 1/2006 | Von Arx et al. |
| 6,993,393 B2 | 1/2006 | Von Arx et al. |
| 7,003,350 B2 | 2/2006 | Denker et al. |
| 7,016,721 B2 | 3/2006 | Lee et al. |
| 7,018,336 B2 | 3/2006 | Enegren et al. |
| 7,024,248 B2 | 4/2006 | Penner et al. |
| 7,027,872 B2 | 4/2006 | Thompson |
| 7,033,322 B2 | 4/2006 | Silver |
| 7,035,684 B2 | 4/2006 | Lee |
| 7,047,065 B2 | 5/2006 | Kalgren et al. |
| 7,060,030 B2 | 6/2006 | Von Arx et al. |
| 7,061,381 B2 | 6/2006 | Forcier et al. |
| 7,088,254 B2 | 8/2006 | Liebenow |
| 7,127,290 B2 | 10/2006 | Girouard et al. |
| 7,130,678 B2 | 10/2006 | Ritscher et al. |
| 7,134,999 B2 | 11/2006 | Brauker et al. |
| 7,136,703 B1 | 11/2006 | Cappa et al. |
| 7,160,252 B2 | 1/2007 | Cho et al. |
| 7,195,594 B2 | 3/2007 | Eigler et al. |
| 7,198,603 B2 | 4/2007 | Penner et al. |
| 7,200,439 B2 | 4/2007 | Zdeblick et al. |
| 7,203,545 B2 | 4/2007 | Schmitt et al. |
| 7,204,798 B2 | 4/2007 | Zdeblick et al. |
| 7,209,790 B2 * | 4/2007 | Thompson et al. ............ 607/60 |
| 7,212,861 B1 | 5/2007 | Park et al |
| 7,214,189 B2 | 5/2007 | Zdeblick |
| 7,225,030 B2 | 5/2007 | Kroll et al. |
| 7,236,821 B2 | 6/2007 | Cates et al. |
| 7,248,923 B2 | 7/2007 | Maile et al. |
| 7,273,457 B2 | 9/2007 | Penner |
| 7,294,105 B1 | 11/2007 | Islam |
| 7,335,161 B2 | 2/2008 | Von Arx et al. |
| 7,392,090 B2 | 6/2008 | Sweeney et al. |
| 7,399,313 B2 | 7/2008 | Brown et al. |
| 7,425,200 B2 | 9/2008 | Brockway et al. |
| 7,452,334 B2 | 11/2008 | Gianchandani et al. |
| 7,481,771 B2 | 1/2009 | Fonseca et al. |
| 2001/0051766 A1 | 12/2001 | Gazdzinski |
| 2002/0023123 A1 | 2/2002 | Madison |
| 2002/0042561 A1 | 4/2002 | Schulman et al. |
| 2002/0045812 A1 | 4/2002 | Ben-Haim et al. |
| 2002/0045836 A1 | 4/2002 | Alkawwas |
| 2002/0049371 A1 * | 4/2002 | Lai et al. ................ 600/300 |
| 2002/0120204 A1 | 8/2002 | Pfeiffer et al. |
| 2002/0126036 A1 | 9/2002 | Flaherty et al. |
| 2002/0147406 A1 | 10/2002 | von Segesser |
| 2002/0151770 A1 | 10/2002 | Noll, III et al. |
| 2002/0183628 A1 | 12/2002 | Reich et al. |
| 2002/0188323 A1 | 12/2002 | Penner et al. |
| 2003/0009204 A1 | 1/2003 | Amundson et al. |
| 2003/0114897 A1 | 6/2003 | Von Arx et al. |
| 2003/0136417 A1 | 7/2003 | Fonseca et al. |
| 2003/0181794 A1 | 9/2003 | Rini et al. |
| 2003/0191383 A1 | 10/2003 | Ben-Haim et al. |
| 2003/0199779 A1 | 10/2003 | Muhlenberg |
| 2004/0032187 A1 | 2/2004 | Penner et al. |
| 2004/0044393 A1 | 3/2004 | Yarden et al. |
| 2004/0064133 A1 | 4/2004 | Miller et al. |
| 2004/0077937 A1 | 4/2004 | Yarden |
| 2004/0122484 A1 | 6/2004 | Hatlestad et al. |
| 2004/0122486 A1 | 6/2004 | Stahmann et al. |
| 2004/0152999 A1 | 8/2004 | Cohen et al. |
| 2004/0158163 A1 | 8/2004 | Cohen et al. |
| 2004/0167416 A1 | 8/2004 | Lee |
| 2004/0172081 A1 | 9/2004 | Wang |
| 2004/0230225 A1 | 11/2004 | Penner et al. |
| 2005/0056539 A1 | 3/2005 | Morgan et al. |
| 2005/0060186 A1 | 3/2005 | Blowers et al. |
| 2005/0065815 A1 | 3/2005 | Mazar et al. |
| 2005/0102002 A1 | 5/2005 | Salo et al. |
| 2005/0124904 A1 | 6/2005 | Roteliuk |
| 2005/0137490 A1 | 6/2005 | Scheiner et al. |
| 2005/0149143 A1 | 7/2005 | Libbus et al. |
| 2005/0154321 A1 | 7/2005 | Wolinsky et al. |
| 2005/0159639 A1 | 7/2005 | Skliar et al. |
| 2005/0159789 A1 | 7/2005 | Brockway et al. |
| 2005/0182330 A1 | 8/2005 | Brockway et al. |
| 2005/0187482 A1 | 8/2005 | O'Brien et al. |
| 2005/0192637 A1 | 9/2005 | Girouard et al. |
| 2005/0192844 A1 | 9/2005 | Esler et al. |
| 2005/0197585 A1 | 9/2005 | Brockway et al. |
| 2005/0215887 A1 | 9/2005 | Ben-Haim et al. |
| 2005/0222631 A1 | 10/2005 | Dalal et al. |
| 2005/0231374 A1 | 10/2005 | Diem et al. |
| 2005/0242479 A1 | 11/2005 | Petisce et al. |
| 2005/0288727 A1 | 12/2005 | Penner |
| 2006/0009818 A1 | 1/2006 | Von Arx et al. |
| 2006/0031378 A1 | 2/2006 | Vallapureddy et al. |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0089694 A1 | 4/2006 | Zhang et al. |
| 2006/0136004 A1 | 6/2006 | Cowan et al. |
| 2006/0142651 A1 | 6/2006 | Brister et al. |
| 2006/0235323 A1 | 10/2006 | Hatib et al. |
| 2007/0043394 A1 | 2/2007 | Zhang et al. |
| 2007/0049977 A1 | 3/2007 | Von Arx et al. |
| 2007/0060959 A1 | 3/2007 | Salo et al. |
| 2007/0129765 A1 | 6/2007 | Gilkerson et al. |
| 2007/0142727 A1 | 6/2007 | Zhang et al. |
| 2007/0161914 A1 | 7/2007 | Zdeblick et al. |
| 2008/0015421 A1 | 1/2008 | Penner |
| 2008/0021333 A1 | 1/2008 | Huelskamp |
| 2008/0021972 A1 | 1/2008 | Huelskamp et al. |
| 2008/0058651 A1 | 3/2008 | Shen et al. |
| 2008/0071178 A1 | 3/2008 | Greenland et al. |
| 2008/0077440 A1 | 3/2008 | Doron |
| 2008/0046037 A1 | 5/2008 | Haubrich et al. |

FOREIGN PATENT DOCUMENTS

| | | |
|---|---|---|
| EP | 0928598 | 7/1999 |
| EP | 1266606 | 12/2002 |
| EP | 1169085 | 8/2004 |
| WO | WO83/03345 | 10/1983 |
| WO | WO 95/03086 | 2/1995 |

| WO | WO 95/27531 | 10/1995 |
| WO | WO97/01986 | 1/1997 |
| WO | WO 97/18856 | 5/1997 |
| WO | WO97/32519 | 9/1997 |
| WO | WO97/33513 | 9/1997 |
| WO | WO97/47236 | 12/1997 |
| WO | WO98/26716 | 6/1998 |
| WO | WO98/29030 | 7/1998 |
| WO | WO99/17095 | 4/1999 |
| WO | WO99/26530 | 6/1999 |
| WO | WO99/34453 | 7/1999 |
| WO | WO99/47205 | 9/1999 |
| WO | WO99/55223 | 11/1999 |
| WO | WO99/55225 | 11/1999 |
| WO | WO99/59460 | 11/1999 |
| WO | WO99/66988 | 12/1999 |
| WO | WO00/16686 | 3/2000 |
| WO | WO00/58744 | 10/2000 |
| WO | WO01/28627 | 4/2001 |
| WO | WO01/56467 | 8/2001 |
| WO | WO01/74278 | 10/2001 |
| WO | WO02/03347 | 1/2002 |
| WO | WO02/32502 | 4/2002 |
| WO | WO03/002243 | 1/2003 |
| WO | WO03/096889 | 11/2003 |
| WO | WO 2005/089638 | 9/2005 |
| WO | WO2005/118056 | 12/2005 |
| WO | WO2006/033812 | 3/2006 |
| WO | WO2006/034183 | 3/2006 |
| WO | WO2006/045073 | 4/2006 |
| WO | WO2006/045074 | 4/2006 |
| WO | WO2006/045075 | 4/2006 |
| WO | WO2006/069215 | 6/2006 |
| WO | WO2007/030474 | 3/2007 |
| WO | WO2007/047287 | 4/2007 |
| WO | WO2007/070794 | 6/2007 |
| WO | WO 2007/099533 | 9/2007 |
| WO | WO 2008/011570 | 1/2008 |
| WO | WO2008/011592 | 1/2008 |
| WO | WO2008/011593 | 1/2008 |
| WO | WO2008/154145 | 12/2008 |

OTHER PUBLICATIONS

B. Henderson et al., "Interaction of Photodynamic Therapy and Hyperthermia: Tumor Response and Cell Survival after Treatment of Mice in Vivo," Cancer Research, vol. 45, 6071 (Dec. 1985).

Bennett et al., "Subcutaneous pressure measurement as a surrogate for an external pressure reference for chronic implantable pressure monitoring," Journal of Cardial Failure, Churchill Livingstone, vol. 9, No. 5, p. S51, Oct. 1, 2003, abstract only.

Bonnefoy E, Ninet J, Robin J, Leroux F, Boissonat P, Brule P, Champsaur G., 1994, Bipolar intramyocardial electrogram from an implanted telemetric pacemaker for the diagnosis of cardiac allograft rejection, Pacing Clin Electrophysiol, 17(11 Pt 2):2052-6.

C. Hierold et al. (Germany, 1998) "Implantable Low Power Integrated Pressure Sensor System For Minimal Invasive Telemetric Patient Monitoring" IEEE, pp. 568-573.

Dipl.-Ing. Torsten Eggers et al. (Germany) "Implantable Telemetric Endosytem (ITES)" IMSAS Institut Fur Mikrosensoren-Aktuatoren Und-Systeme, 1998. 2 pp.

E R. Cosman et al. (Massachussetts, Apr. 1979) "A Telemetric Pressure Sensor for Ventricular Shunt Systems" Surgical Neurology vol. 11, No. 4, pp. 287-294.

G.W.H. Schurink et al. (1998) "Late Endoleak After Endovascular Therapy for Abdominal Aortic Aneurysm" Eur. J. Vasc. Endovasc. Surg. vol. 17, pp. 448-450.

Gerhausser A, Reichel T, Neukomm P A, Bolz A, Hugel J, Schaldach M, 1997, Diagnosis of rejection after kidney transplantation by impedance spectroscopy with an implantable measuring system, Biomed Tech (Berl), 42 Suppl. 160-1.

GH White et al. (1997) "Endoleak Following Endoluminal Repair of AAA: Management Options and Patient Outcomes", J. Endovasc Surg, pp. 1-45.

Graichen et al., "Patient Monitoring System for Load Measurement with Spinal Fixation Devices," Med. Eng. Phys. 18, (1996), pp. 167-174.

Haas et al., "Photodynamic Effects of Dyes on Bacteria," Published in Mutation Research, 1979, vol. 60, pp. 1-11.

Hashima et al., "Nonhomogenous Analysis of Epicardial Strain Distributions During Acute Myocardial Ischemia in the Dog," J Biomech 1993, Jan 26: 19-35.

Hetzer R. et al., 1998, Daily non-invasive rejection monitoring improves longterm survival in pediatric heart transplantation, Ann. Thorac. Surg. (66):1343-1349.

J.A. Parrish, "Photobiologic Consideration on Photoradiation Therapy," pp. 91-108, Porphyrin Photosensitization, Plenum Press, (1983).

K.E. Uhrich et al., "Synthesis and characterization of degradable poly(anhydride-co-imides)", Macromolecules, 1995, 28, 2184-93.

Karl E. Richard et al. (Germany, Jan. 1999) "First clinical results with a telemetric shunt-integrated ICP-sensor" Neurological Research vol. 21, pp. 117-120.

Labrousse and Satre, "Photodynamic Killing of Dictyostelium Discoideum Amoebae Mediated by 4',5'-Diiodoflurescin Isothiocyanate Dextran. A strategy for the isolation of Thermoconditional Endocytosis Mutants," published in Photochemistry and Photobiology, 1993, vol. 67, No. 3, pp. 531-537.

Mackay et al., "Bio-medical Telemetry: Sensing and Transmitting Biological Information from Animals and Man," John Wiley & Sons, Inc. New York (1970) pp. 244-245.

Pfitzmann R, Muller J, Grauhan O. Cohnert T, Hetzer R, Z Kardiol, 1998, Measuring bioelectric myocardial impedance as a non invasive method for diagnosis of graft rejection after heart transplantation, 87(4):258-266.

Pirolo J S, Shuman T S, Brunt E M, Liptay M J, Cox J L, Ferguson T B Jr., J Thoracic Cardiovasc Surg, 1992, Noninvasive detection of cardiac allograft rejection by prospective telemetric monitoring, 103(5):969-79.

Prof. Dr. Johannes Zacheja et al. (Germany, Sep. 1996) "An Implantable Microsystem For Biomedical Applications" Micro System Technologies 96, pp. 717-722.

S.K. Gupta et al. (1999) "Use of a Piezoelectric Film Sensor for Monitoring Vascular Grafts", The American Journal of Surgery, vol. 160, pp. 182-186.

T. Chuter et al. (Sweden, Jan. 1997) "Aneurysm Pressure Following Endovascular Exclusion" Eur. J. Vasc. Endovasc. Surg. vol. 13, pp. 85-87.

T.A. Cochran et al. (1990) "Aortic Aneurysm Abdominal", Current Therapy in Adult Medicine, Fourth Edition.

Z. Tang et al. (May 1995) "Data Transmission from an Implantable Biotelemeter by Load-Shift Keying Using Circuit Configuration Modulator" IEEE Transactions on Biomedical Engineering. vol. 42, No. 5, pp. 524-528.

Fink, Mathias, "Time Reversal of Ultrasonic Fields—Part I: Basic Principles", IEEE Transactions on Ultrasonics, Ferroelectrics, and Frequency Control, vol. 39, No. 5, Sep. 1992, pp. 555-566.

Wu, Francois et al., "Time Reversal of Ultrasonic Fields—Part II: Experimental Results", IEEE Transactions on Ultrasonics, Ferroelectrics, and Frequency Control, vol. 39, No. 5, Sep. 1992, pp. 567-578.

Strickberger, S. Adam et al., "Extracardiac Ablation of the Canine Atrioventricular Junction by Use of High-Intensity Focused Ultrasound", Circulation, Jul. 13, 1999; downloaded from circ. ahajournals.org at ACS/GUIDANT on Jan. 4, 2008, pp. 203-208.

Bourgeois, Maurice J. et al., "Continuous Determination of Beat-to-Beat Stroke Volume from Aortic pressure Pulses in the Dog", Circulation Research, vol. 39, pp. 15-24 (1976).

Rozenman, Yoseph et al., "Wireless Acoustic Communication With A Miniature Pressure Sensor in the Pulmonary Artery for Disease Surveillance and Therapy of Patients With Congestive Heart Failure", Journal of the American College of Cardiology, 49:7, 2007, pp. 784-789.

Wesseling, KH et al., "Computation of Aortic Flow From Pressure In Humans Using a Nonlinear, Three-Element Model", Journal of Applied Physiology, vol. 74, Issue 5, pp. 2566-2573 (1993).

Cohen, T.J. et al., "A Hemodynamically Responsive Antitachycardia System. Development and Basis for Design in Humans", Circulation 1990, vol. 82, No. 2, pp. 394-406, XP002560584.

Blacher, Jacques et al., "Aortic Pulse Wave Velocity as a Member of Cardiovascular Risk in Hypertensive Patients", Hypertension May 1999;33;1111-1117.

Farzaneh-Far, Ramin et al., Usefulness of Noninvasive Estimate of Pulmonary Vascular Resistance to predict Mortality, Heart Failure, and Adverse Cardiovascular Events in Patients With Stable Coronary Artery Disease (from the Heart and Soul Study), The American Journal of Cardiology, vol. 101, Issue 6, Mar. 15, 2008, pp. 762-766.

El Gamal, M.I.H. et al., "Chronic Ventricular Pacing With Ventriculo-Atrial Conduction Versus Atrial Pacing in Three Patients With Symptomatic Sinus Bradycardia", PACE, vol. 4, Jan.-Feb. 1981, pp. 100-106.

Fujiki, Akira et al., "Pacemaker Syndrome Evaluated by Cardiopulmonary Exercise Testing", PACE, vol. 13, Oct. 1990, pp. 1236-1241.

* cited by examiner

IMPLANTED SENSOR SYSTEM WITH OPTIMIZED OPERATIONAL AND SENSING PARAMETERS

RELATED APPLICATION DATA

The present application claims the benefit of priority under 35 U.S.C §119 to U.S. Provisional Application 60/630,910, filed Nov. 24, 2004.

FIELD OF INVENTION

The present invention relates generally to the field of diagnostic and therapeutic medical implants and, more particularly implanted biological sensor systems.

BACKGROUND

Inplantable devices for sensing physiological parameters (e.g., pressure or flow rate in a blood lumen) are known, e.g., an implanted sensor system configured to sample a physiological signal at an implantation site in a body. In order to retrieve clinic information from the sampled physiological signal, the original signal has to be sampled with sufficient accuracy and rate. The key operating parameters for sampling include: the sampling time, i.e., when is the signal sampled, the time span between the first and last measurement, whether the signal is quasi-periodic, when (within the sample period) the signal measured, the sampling rate, the measurement range (e.g. the minimum and maximum signal values that the sensor may sense), and the signal resolution (e.g. the minimal change in signal magnitude that would alter the resulting reading).

If the sensor includes a trigger mechanism, e.g. start to sample when the signal level goes below a threshold, then the parameters of the trigger mechanism also affect the quality of the measurements and the resources needed to generate them. When operated with the most stringent values for these parameters, the sensor may provide clinically relevant information, but the resources required to obtain such information may be too high, especially power consumption, but also in terms of the size, complexity, and throughput.

If the sensor is embedded in an implant, and especially if this implant operates using an acoustic switch, then sampling may take a significant proportion of the power budget of the implant. Since the sensor consumes practically no power when idle, most of its power budget is allocated to taking measurements. The more measurements it takes per exam, the fewer exams it can perform. An exam is a term used to measure a physiologically relevant value at a given point of time, for instance, systemic blood pressure. The resolution relates to the number of sampled bits. Sampling at higher resolution (for example, 1000 distinct signal levels) would require more power than sampling at lower resolution. When the signal range is diminished, one can reduce the number of distinct signal levels and keep the resolution, and thus save power.

Saving power is only one part of the problem. When optimizing the sampling parameters, one can sample fewer measurements, and thus require a smaller buffer to hold them. If the samples are transmitted to a medical system, either extracorporeal or implanted, the transmission bandwidth may be limited. Sampling fewer measurements may enable transmission that would otherwise not be possible. Reducing the signal range that the sensor needs to sample may reduce the size, cost, and complexity of the sensor.

SUMMARY OF EMBODIMENTS OF THE INVENTION

Embodiments of the invention are directed to an implantable sensor system that samples a physiological signal at an implantation site in a body. In one embodiment, a system is provided where the implanted sensor is controlled by another device. The other device may be another implanted medical device, or an external system. The control of, and communication with, the implanted sensor may be via a wired or wireless link. If the control device has additional information that is dynamically changing and which may affect the operation of the implanted sensor, optimized operation of the implanted sensor may be accomplished by transferring this information, or derivatives of this information, to the implanted sensor.

The sensor may be, by way of non-limiting example, a pressure sensor, and more specifically a sensor configured to measure hemodynamic pressure in a blood vessel. Other sensors may include, by way of further non-limiting examples, an electrocardiogram (ECG) sensor or an echo signal, an accelerometer, and sensors that measure physiological characteristics such as heart contractility, cardiac output, blood flow, oxygen saturation, glucose concentration, position of an orthopedic implant, radiation or temperature.

The dynamic side information, by which the medical device makes "decisions" regarding the operating parameters of the implanted sensor, can be of many sources. For example, the side information can come not only from a sensor but also from an operation performed by the medical device, such as neuro-activation, electrical signaling, pacing, and/or releasing or pumping of a drug into the body.

DETAILED DESCRIPTION OF EMBODIMENTS

Knowledge of the Pressure Range

In hemodynamic monitoring, the pressure measured by the implanted pressure sensor is referenced to the barometric pressure. If the controlling unit knows the barometric pressure, it can direct the implant to measure the pressure at the vicinity of this pressure. By way of examples, the controlling unit may be an external unit with access to a barometer, or an internal unit that has access to the barometric measurement information. This reduces the pressure range that the implant needs to be able to measure, and for a given resolution, may save on power consumption.

Figure 1:
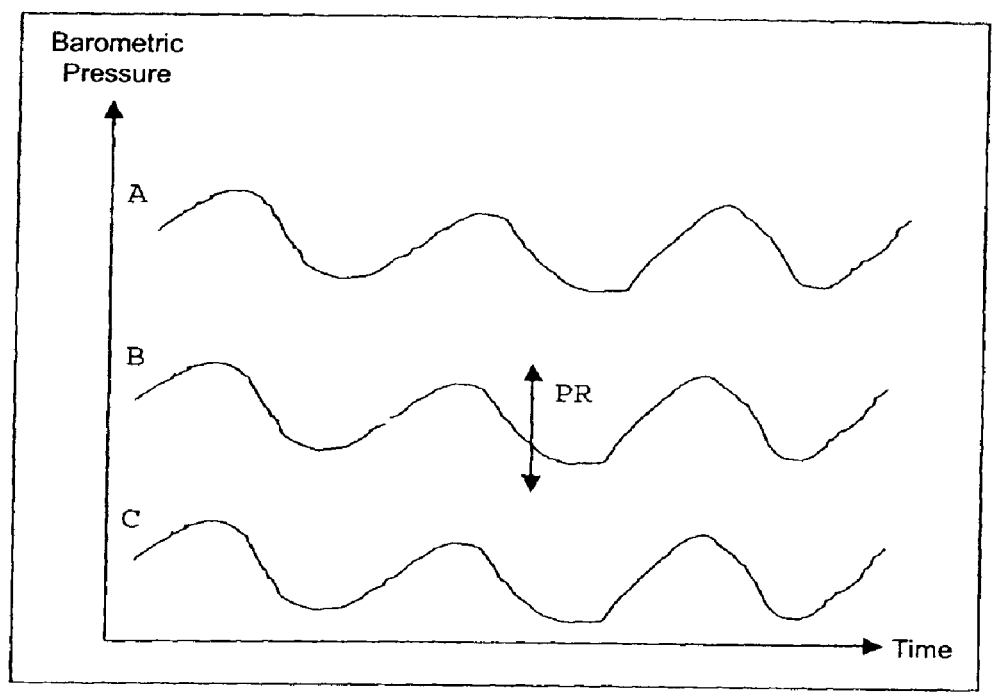
FIG. 1 shows pressure signals as seen by the implant for external barometric pressure signals at sea level, 1 km, and 2 km height

FIG. 1 shows the pressure signal as seen by the implant in three different cases, designated as A, B and C. The three cases differ in the external barometric pressure, for instance at sea level, 1 km height, and 2 km height. If the barometric pressure is known to be close to signal B, the pressure range described by the arrow "PR" can be conveyed to the pressure sensor implant. This will only have to sample at this pressure range, improving its accuracy for a given power, or improving power consumption for a given accuracy.

Knowledge of the Change Rate

It is well known that a rapidly changing signal has to be sampled at higher rate than a slowly changing signal. In hemodynamic pressure measurement application, if the control unit has access to the heart rate, the pressure sensor can be provided with the heart rate information, or its derivative, and adjust the sampling rate accordingly. The control unit may estimate the rate of change of the heart signal using electro cardio gram signal (ECG).

Knowledge of the Signal Phase

Further optimization is possible when the phase of the pressure signal is known. For example, if the system is interested in the pressure value of the diastole, if the time of the diastole can be estimated from an ECG signal, then the time when the diastole will be sensed by the pressure sensor may be estimated. This is true for many locations where the pressure sensor may be positioned, for instance, the pulmonary artery, iliac artery, femoral artery, renal artery, aorta, subclavian artery, carotid artery. The control unit then can provide the pressure sensor with information when to sample, as well as the other operating parameters for most efficient measurement.

Figure 2:
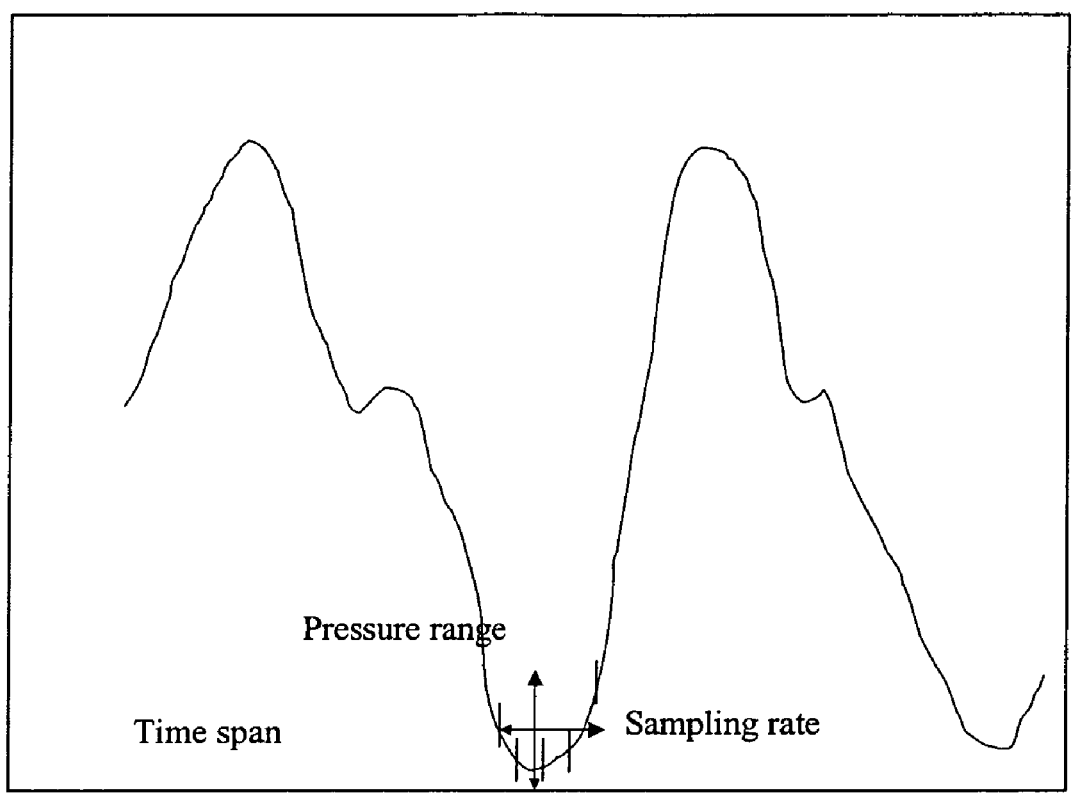
FIG. 2 illustrates a pressure signal during diastole

FIG. 2 depicts a schematic illustration of a pressure signal going through the diastole. The arrows show that the time span, sampling rate, pressure range may all be adjusted to the signal at hand.

Triggering

Figure 3:
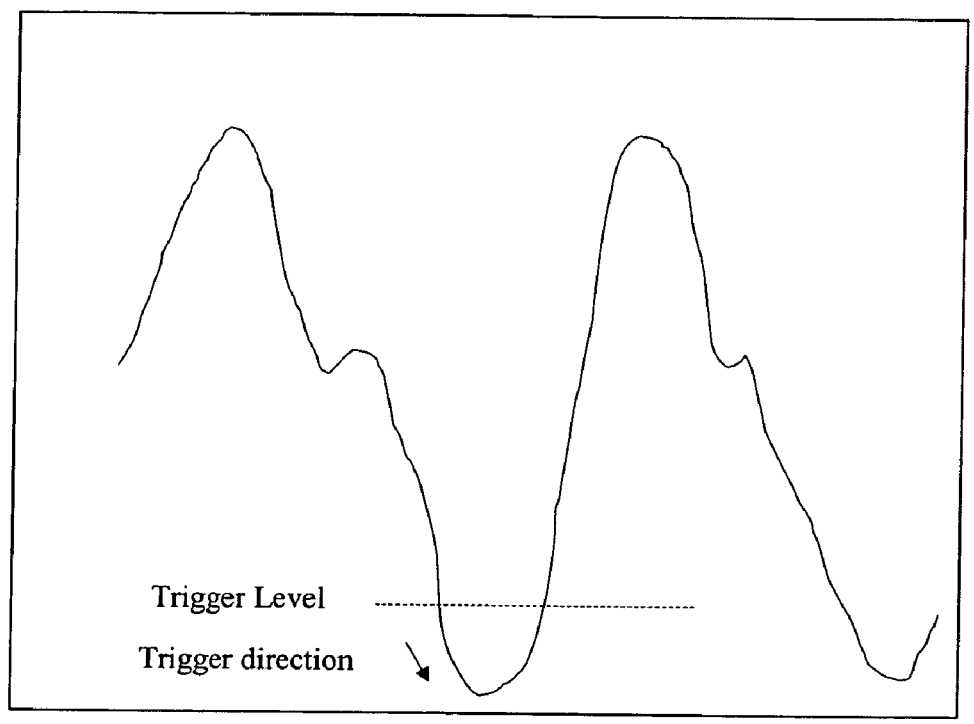
FIG. 3 illustrates performing an accurate measurement on sensed pressure FIG. 4 describes a system having a control unit with sensors for measuring physiological signals

If the coarse level of the signal is known, the sensor may be optimized by dynamically providing it with trigger parameters. For example, if the device measures pressure using a coarse sensor, it may estimate the level and direction where a trigger should be set at the implanted pressure sensor. By dynamically providing the pressure sensor with such information, the pressure sensor may then perform an accurate measurement at the exact spot, as is shown in FIG. 3.

Other Signals

Figure 4:
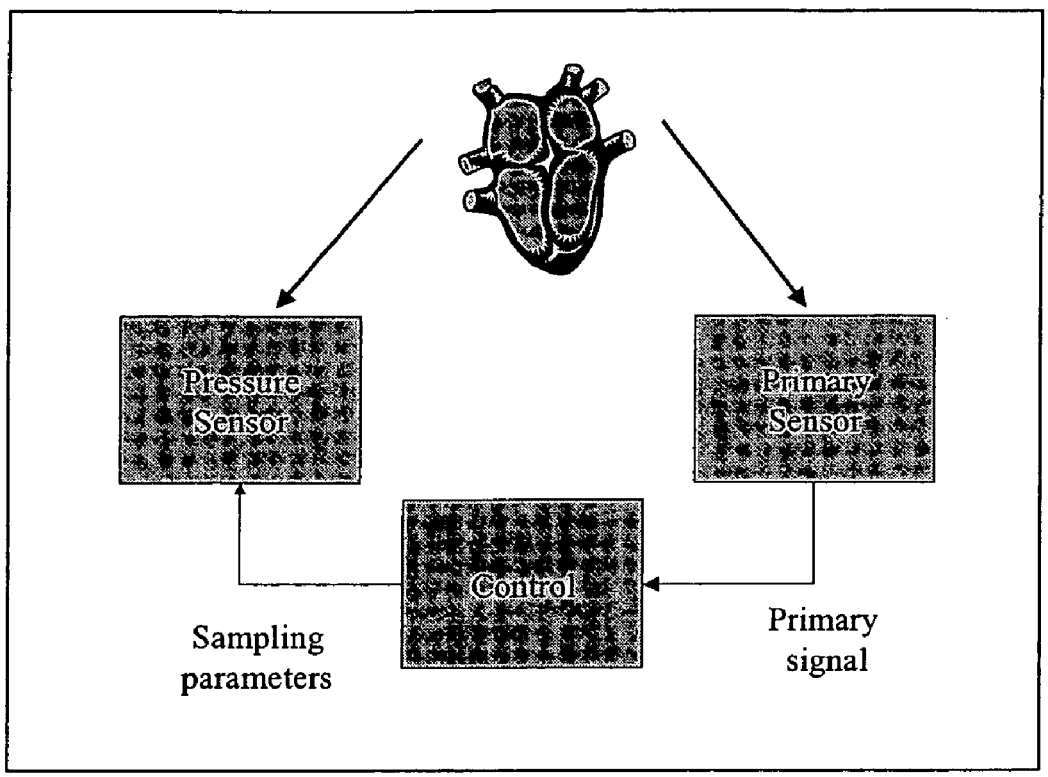

With reference to FIG. 4, a system is disclosed in which the control unit may is an implanted medical device that has access to a physiological signal. One example is an electro cardiac signal. Other possible signals include an echo signal, accelero-metric signal, a pressure signal taken at a different location, optical signal, and others. The information extracted from the primary signal is transferred directly, or using a derivative, to the pressure sensor.

Specific Example

A specific example may be where the ECG and control unit are part of an implantable pulse generator ("IPG"), or cardiac resynchronization therapy ("CRT") device, and the pressure sensor is distinct. The pressure sensor may be connected to an IPG using a wired or wireless (e.g., acoustic) communication link. The sampling time may be passed to the pressure sensor as a trigger. Alternatively, it may be passed as a time signal, when both implants keep synchronized clocks. This alleviates possible problems when the communication link between the implants may drop a message. The heart rate may be passed directly, or may be passed as a parameter, indicating the required sampling rate. The pressure range and resolution may be passed directly, or as a parameter Other Communication Methods The communication between the pressure sensor and the other medical device could be acoustic. However, if reasonable electromagnetic link exists between the modules, the communication can also be using electric field or magnetic field. This is especially true of both devices are close to the skin. The communication can be directly between the devices or through one or more devices, forwarding the messages between them.

Example with Thermal Therapy and a Thermal Sensor

During thermal therapy, the external system knows the expected thermal profile at the location of the sensor, and can inform the implant regarding the range.

Example with Oxygen Saturation

Oxygen saturation can be measured during the systole, where the diameter of the artery is maximal. This improves the quality of the measurement. By providing this information to the oxygenation meter (when to sample, and what expected range), the power and accuracy may be optimized.

What is claimed is:

1. A medical system for sensing pressure within a blood lumen of a body having a heart, the system comprising:
   an implantable pressure sensor capable of generating an analog blood pressure signal indicative of blood pressure within the lumen; and
   an implantable medical device in communication with the pressure sensor, the medical device including an electrocardiogram sensor configured to sense an electrocardiogram signal within the body and determine a rate of the heart, and a control unit configured to determine a sampling rate parameter of the pressure sensor based on the rate of the heart and transmit the sampling rate parameter to the pressure sensor;
   wherein the implantable pressure sensor is configured to adjust the rate at which the analog blood pressure signal is digitized based at least in part on the sampling rate parameter received from the medical device.

2. The system of claim 1, wherein the medical device is selected from the group comprising a pacemaker, a cardioverter defibrillator ("ICD") device, a cardiac resynchronization therapy ("CRT") device, a CRT-pacemaker combination device, a CRT-ICD combination device, a nerve stimulator, a drug pump, and an insulin pump.

3. The system of claim 1, wherein the pressure sensor is attached to an anchoring device configured for implantation in one or more of an artery, a heart ventricle, a heart atrium, a vein, a heart valve, and a bypass graft.

4. The system of claim 1, wherein the medical device is an extracorporeal device.

5. The system of claim 1, wherein the medical device is configured for communicating with the implantable sensor via a wired communication link.

6. The system of claim 1, wherein the medical device is configured for communicating with the implantable sensor via a wireless communication link.

7. The system of claim 6, wherein the wireless communication link is selected from the group comprising acoustic communication, radio-frequency communication, and electro-magnetic communication.

8. The system of claim 1, wherein the medical device is configured to determine a sampling time span.

9. The system of claim 1, wherein the medical device is configured to determine a sampled signal magnitude range.

10. The system of claim 1, wherein the medical device is configured to determine a trigger for initiating sampling of the pressure sensor.

11. The system of claim 10, wherein the medical device is configured to determine one or both of a sampling trigger level and a sampling trigger direction.

12. A medical system for sensing pressure within a blood lumen of a body having a heart, the system comprising:

an implantable pressure sensor capable of generating an analog blood pressure signal indicative of blood pressure within the lumen; and an implantable medical device in acoustic communication with the pressure sensor, the medical device including an electrocardiogram sensor configured to sense an electrocardiogram signal within the body and determine a rate of the heart, and a control unit configured to determine a sampling rate parameter of the pressure sensor based on the rate of the heart and acoustically transmit the sampling rate parameter to the pressure sensor;

wherein the implantable pressure sensor is configured to adjust the rate at which the analog blood pressure signal is digitized based at least in part on the sampling rate parameter received from the medical device.

13. The system of claim 12, wherein the medical device is selected from the group comprising a pacemaker, a cardioverter defibrillator ("ICD") device, a cardiac resynchronization therapy ("CRT") device, a CRT-pacemaker combination device, a CRT-ICD combination device, a nerve stimulator, a drug pump, and an insulin pump.

14. The system of claim 12, wherein the pressure sensor is attached to an anchoring device configured for implantation in one or more of an artery, a heart ventricle, a heart atrium, a vein, a heart valve, and a bypass graft.

15. The system of claim 12, wherein the medical device is an extracorporeal device.

16. The system of claim 12, wherein the medical device is configured to determine a sampling time span.

17. The system of claim 12, wherein the medical device is configured to determine a sampled signal magnitude range.

18. The system of claim 12, wherein the medical device is configured to determine a trigger for initiating sampling of the pressure sensor.

19. The system of claim 12, wherein the medical device is configured to determine one or both of a sampling trigger level and a sampling trigger direction.

\* \* \* \* \*